United States Patent
Rock

(10) Patent No.: US 6,480,272 B1
(45) Date of Patent: Nov. 12, 2002

(54) SYSTEM AND METHOD FOR IN-SITU PARTICLE CONTAMINATION MEASUREMENT USING SHADOWGRAMS

(75) Inventor: David F. Rock, Torrance, CA (US)

(73) Assignee: Raytheon Company, Lexington, MA (US)

( * ) Notice: Subject to any disclaimer, the term of this patent is extended or adjusted under 35 U.S.C. 154(b) by 23 days.

(21) Appl. No.: 09/947,797

(22) Filed: Sep. 6, 2001

(51) Int. Cl.[7] .............................................. G01N 21/00
(52) U.S. Cl. ............................. 356/237.2; 356/237.3; 356/239.2; 356/398
(58) Field of Search .......................... 356/237.1, 237.2, 356/237.3, 237.4, 237.5, 237.6, 239.1, 239.2, 239.3, 356, 337, 339, 340–343, 388, 398, 338; 250/574, 575

(56) References Cited

U.S. PATENT DOCUMENTS

| | | | | |
|---|---|---|---|---|
| 4,893,932 A | * | 1/1990 | Knollenberg | 356/237.2 |
| 5,359,407 A | * | 10/1994 | Suzuki et al. | 356/237.1 |
| 6,295,126 B1 | * | 9/2001 | Miyazaki et al. | 356/237.5 |
| 6,314,200 B1 | * | 11/2001 | Nakayama et al. | 356/239 |

FOREIGN PATENT DOCUMENTS

| | | | |
|---|---|---|---|
| EP | 0714 157 A2 | * | 5/1996 |
| JP | 10 62348 | * | 3/1998 |

* cited by examiner

Primary Examiner—Frank G. Font
Assistant Examiner—Sang H. Nguyen
(74) Attorney, Agent, or Firm—Colin M. Raufer; Leonard A. Alkov; Glenn H. Lenzen, Jr.

(57) ABSTRACT

A system (100) for determining particle contamination on optical surfaces (112, 114, 116) includes a detector array (118) and a non-coherent light source (110) that illuminates the detector array with non-coherent light reflected or refracted by the optical surfaces. Processing equipment (134) identifies shadows (302, 402, 502) on the detector array which are indicative of particle contamination of the optical surfaces. A light source controller (130) moves the non-coherent light source resulting in movement of the shadows on the detector array. The processing equipment distinguishes shadows caused by particle contamination on a first of the optical surfaces (112) from shadows caused by particle contamination on the other optical surfaces (114, 116) based on the movement of the shadows. The system also includes a particle contamination level analyzer (128) to estimate a particle contamination level for each optical surface from contrast levels of the shadows identified for each optical surface.

28 Claims, 5 Drawing Sheets

SYSTEM AND METHOD FOR IN-SITU PARTICLE CONTAMINATION MEASUREMENT USING SHADOWGRAMS

FIELD OF THE INVENTION

The present invention pertains to detection of particle contamination on an optical surface, and in particular to in-situ measurement of particle contamination on optical surfaces.

BACKGROUND

High quality, precision optical equipment often cannot perform to its optimum capabilities when its surfaces are contaminated with particles, such as dust. For example, one possible requirement of optical space surveillance sensors is to detect low-radiance targets in the presence of intense out-of-field sources, such as the Earth and sun. This requirement places high demands on system capabilities requiring very low scatter optical surfaces to be used for elements of the optical path. Contamination particles which are deposited on the optical surfaces during fabrication, sensor testing, storage, launch, deployment or operation, may significantly reduce system performance resulting in reduced signal levels and unacceptable signal to noise performance due to the scattering and extinction of light caused by the contamination particles.

One technique used to measure particle contamination on an optical surface utilizes a strip of adhesive tape to lift particles off the optical surface. The size and distribution of particles are then evaluated under a microscope. One disadvantage to this technique is that as the optical system comes together during the assembly phases, the optical surface becomes inaccessible. Another disadvantage to this technique is that it cannot be used in the field or on remote platforms, such as optical space surveillance sensors or space based telescopes.

Another technique used to measure particle contamination on an optical surface uses a detector to measure light scattered from the contamination particles on the optical surface. A light source illuminates a portion of the optical surface and either the light source or the detector is moved to measure the scatter from the particles at various angles. The angular dependence of the scatter is used to estimate the particle contamination level of the optical surface. One problem with this technique is that it can be used to measure the particle contamination of only one optical surface and is not particularly useful in systems that include several optical surfaces. Another problem with this technique is that it does not distinguish very well between scatter cause by particle contamination and scatter caused by micro-roughness of the optical surface. Another problem with this technique is that it is difficult to suppress spurious stray light paths that can invalidate the scatter measurements.

Thus, there is general need in the art for an improved system and method for determining particle contamination levels on optical surfaces. There is also a general need in the art for a system and method for determining particle contamination on inaccessible optical surfaces of optical systems such as remotely located space surveillance sensors or remote platforms, or on satellites with optical sensors or telescopes. There is also a general need in the art for a system and method for determining particle contamination on each of the various optical surfaces of systems that employ several optical surfaces.

SUMMARY OF THE INVENTION

The need in the art is addressed by the various embodiments of the present invention which provide a system and method for measuring particle contamination on optical surfaces. In one embodiment, the system includes a detector array, a non-coherent light source that illuminates the detector array with non-coherent light reflected by the optical surfaces, and processing equipment that analyzes shadows on the detector array. The shadows are indicative of particle contamination of the optical surfaces. In this embodiment, the system also includes a light source controller that changes the position of the non-coherent light source. The processing equipment distinguishes shadows caused by particle contamination on a first of the optical surfaces from shadows caused by particle contamination on the other optical surfaces based on movement of the shadows. The system also includes a particle contamination level analyzer that estimates an average particle contamination level for the optical surfaces based on contrast levels of the shadows identified for each optical surface.

In another embodiment of the present invention, a system for measuring particle contamination on refractive optical surfaces is provided. In another embodiment, a plurality of non-coherent light sources separately illuminate the detector array to produce sets of shadows on the detector caused by particle contamination on the each of the optical surfaces. In this embodiment, the shadows of a first set are distinguished from shadows of a second set by identifying different changed positions for the shadows which result from separate illumination of each non-coherent light source of the plurality.

In yet another embodiment of the present invention, a method for measuring particle contamination levels on optical surfaces is provided. The method includes illuminating a detector array with light reflected or refracted by the optical surfaces from a non-coherent light source, and identifying shadows on the detector array. In this embodiment, the method includes changing a position of the non-coherent light source to distinguish shadows caused by the particles on each of the optical surfaces, and estimating an average particle contamination levels for each of the optical surfaces based on contrast levels of the shadows identified for each optical surface.

BRIEF DESCRIPTION OF THE DRAWINGS

The invention is pointed out with particularity in the appended claims. However, a more complete understanding of the present invention may be derived by referring to the detailed description when considered in connection with the figures, wherein like reference numbers refer to similar items throughout the figures and:

The description set out herein illustrates the various embodiments of the invention and such description is not intended to be construed as limiting in any manner.

DETAILED DESCRIPTION OF THE DRAWINGS

The present invention relates to systems and methods for determining particle contamination on optical surfaces. In the various embodiments, the present invention provides for the measurement of particle contamination on accessible optical surfaces, as well as inaccessible optical surfaces. For example, particle contamination can be measured on optical surfaces of remotely located sensors or optical systems of orbiting satellites. The present invention, in one embodiment, provides particle contamination measurements for each of several optical surfaces in systems that include more than one optical surface. The present invention, in another embodiment, compensates for the particle contamination levels measured on the optical surfaces, for example, to achieve improved system performance. In yet another embodiment, the present invention provides for cleaning the optical surfaces when particle contamination levels exceed a predetermination level, for example, to improve system performance.

In accordance with one embodiment, a system for determining particle contamination on reflecting optical surfaces includes a detector array and a non-coherent light source to illuminate the detector array with non-coherent light reflected by the optical surfaces. In accordance with another embodiment, a non-coherent light source illuminates the detector array with non-coherent light refracted by refracting optical surfaces. In these embodiments, processing equipment identifies shadows on the detector array which are indicative of particle contamination of the optical surfaces. A light source controller moves the non-coherent light source. The processing equipment distinguishes shadows caused by particle contamination on a first of the optical surfaces from shadows caused by particle contamination on the other optical surfaces based on movement of the shadows. In this embodiment, the system also includes a particle contamination level analyzer that estimates an average particle contamination level for each optical surface based on contrast levels of the shadows identified for each optical surface. Although the present invention is generally described for use with reflective optical surfaces, in the various embodiments, it is equally applicable for use with refractive optical surfaces and combinations of both reflective and refractive optical surfaces.

Figure 1:
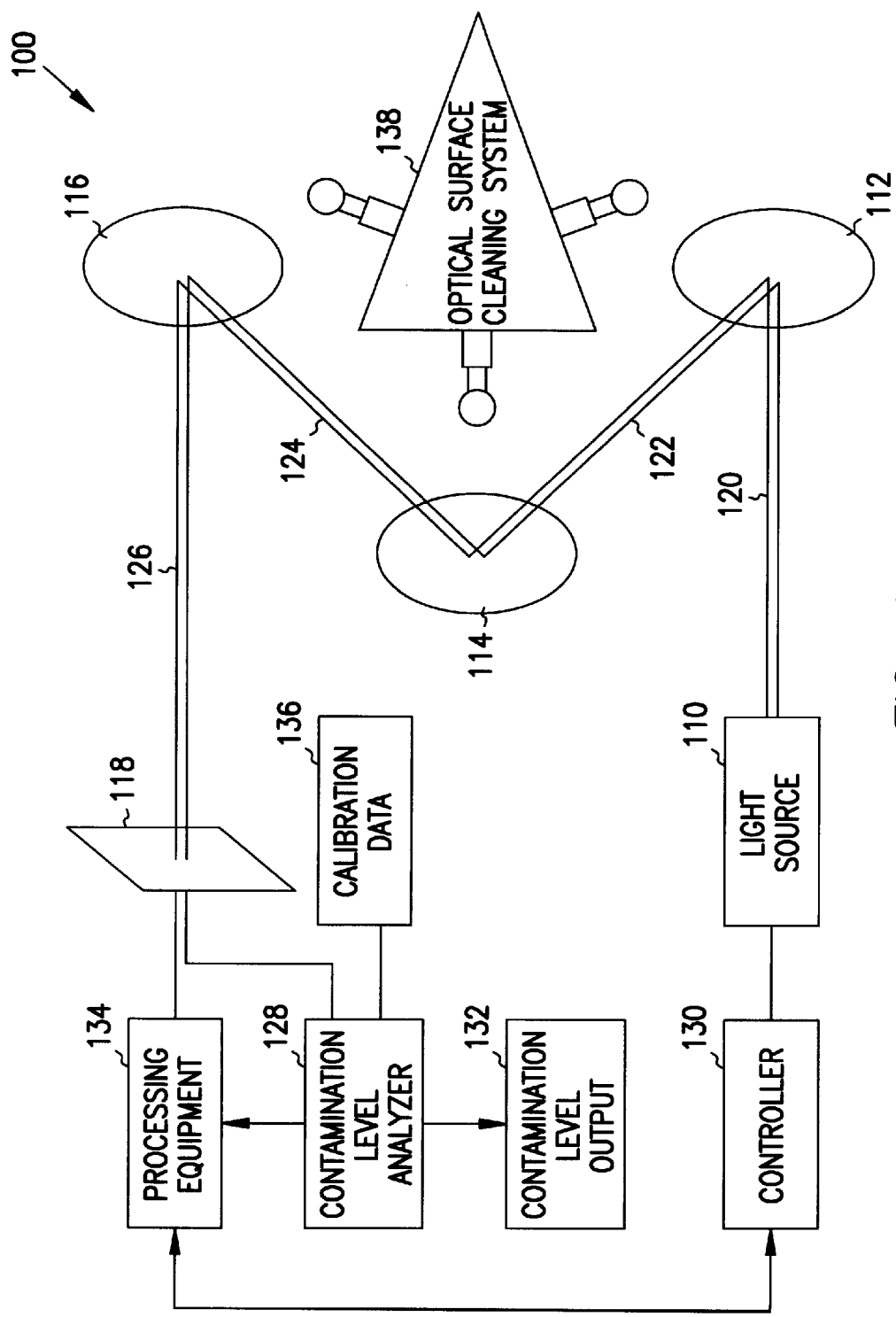
FIG. 1 illustrates a simplified functional configuration of an optical system in accordance with an embodiment of the present invention.

FIG. 1 illustrates a simplified functional configuration of an optical system in accordance with an embodiment of the present invention. System 100 includes portions that may be part of optical systems that are remotely located or inaccessible. Alternately, system 100 may include portions that may be part of optical systems used for measurement and calibration purposes and not part of an end-use optical system.

Optical system 100 includes first optical surface 112, second optical surface 114 and third optical surface 116 configured to focus light on detector array 118. First, second and third optical surfaces 112, 114, 116 may be any reflective optical surface including mirrors or other highly reflective surfaces, and may include curved as well as flat surfaces. In one embodiment, optical surfaces 112, 114 and 116 comprise mirrors having a diameter between eight and twelve inches, although larger and smaller diameter optical surfaces are also suitable for use with the various embodiments of the present invention. In an alternate embodiment (not shown), first, second and third optical surfaces 112, 114, 116 may be any refractive optical surface such as lenses or other refractive surfaces, and may include curved as well as flat optical surfaces.

Detector array 118 is a two-dimensional light detection array located at a focal plane of the optical surfaces. Detector array 118 may be comprised of individual light detectors such as charge coupled devices (CCDs). The individual light detectors on detector array 118 are desirably spaced apart a distance on the order of ten microns or so. First, second and third optical surfaces 112, 114, 116 are configured to provide a path for light reflected by each optical surface to be focused on detector array 118. As illustrated, a light path comprises a first portion 120 which passes light rays to first optical surface 112, a second portion 122 which passes light rays reflected by first optical surface 112 to second optical surface 114, a third portion 124 which passes light rays reflected by second optical surface 114 to third optical surface 116, and a fourth portion 126 which passes light rays reflected by third optical surface 116 to detector array 118. Light path portions 120, 122, 124 and 126 are generally empty spaces between the optical elements of the system through which light rays pass. Although system 100 is illustrated with three optical surfaces, the embodiments of the present invention are applicable to systems having a single optical surface to systems having many more than three optical surfaces.

Light source 110 is used to illuminate detector array 118 allowing system 100 to perform particle contamination level measurements as described herein. Light source 110 may be a small non-coherent light source, such as a point light source. In alternate embodiments, light source 110 may comprise a small array of non-coherent point light sources located, for example, on a strut coupled to first optical surface 112. Although the various embodiments of the present invention are described for the use of non-coherent light sources, it should be noted that other types of non-coherent radiation are also suitable for use with the present invention.

In the illustrated embodiment, first, second and third optical surfaces 112, 114, 116 may form part of an optical system, such as a telescope or optical sensor, that receives incoming light from an aperture (not shown) and focuses the incoming light on a detector array such as detector array 118. Detector array 118 may be used for particle contamination measurements as described herein, in addition to such operational use. Alternatively, separate detector arrays may be provided for operational use and/or particle contamination measurements.

In an alternate embodiment, first, second and third optical surfaces 112, 114, 116 are refractive optical surfaces such as lenses. Detector array 118 is located behind the optical surfaces to focus light rays traveling through the optical surfaces.

To perform particle contamination measurements, light source 110 illuminates detector array 118 with non-coherent light that is reflected by the first, second and third optical surfaces. Light source 110 is positioned at a short distance from the optical surfaces such that particles and imperfections on the optical surfaces produce shadows on detector array 118. Contamination particles, for example, produce shadows that when viewed on a display, look like spots of varying contrast. Shadows of greater contrast result from larger contamination particles on the optical surfaces, or result from larger imperfections on one of the optical surfaces. Processing equipment 134 processes signals from the elements of detector array 118 to identify the shadows of varying contrast levels and contamination level analyzer 128 compares the spots of various contrast levels with calibration data 136 to estimate particle contamination levels of the optical surfaces as well as the sizes of the particles on the optical surfaces. Contamination level analyzer 128 may also provide the average particle contamination level as contamination level output 132.

In one embodiment of the present invention, the process of measuring particle contamination on optical surfaces is used in system 100 during a system assembly process to determine particle contamination levels prior to system deployment. In this case, optical surface cleaning system 138 may be employed to clean the optical surfaces prior to final assembly. In another embodiment, processing equipment 134 may use the particle contamination measurements to calibrate out the effects of the particle contamination.

In another embodiment of the present invention, processing equipment 134 processes optical signals in the field and uses the estimated average particle contamination level of the optical surfaces to compensate the system output. In other words, processing equipment 134 attempts to calibrate out the effects of the particle contamination to achieve improved system performance. In this embodiment of the present invention, system 100 may perform particle contamination measurements in the field on a regular basis, and re-compensate the system output due to changes in measured particle contamination levels. For example, when system 100 is part of a remotely located space based sensor or telescope, the optical surfaces over time may experience increased particle contamination. In this embodiment, system 100 performs particle contamination measurements and attempts to calibrate out the effects of the changes in particle contamination. In another embodiment, optical surface cleaning system 138 may clean the optical surfaces in the field when particle contamination exceeds certain predetermined levels. Optical surface cleaning system 138 may, for example, use a carbon-dioxide jet spray or plasma cleaning process.

In accordance with the various embodiments of the present invention that measure particle contamination on more than one optical surface, system 100 includes light source controller 130. Light source controller 130 changes the position of light source 110 relative to the optical surfaces to produce changes in the position of the shadows on detector array 118 resulting from contamination particles on the optical surfaces. As light source controller 130 moves light source 110, shadows produced by contamination particles on first optical surface 112 may move at a first rate, shadows produced by contamination particles on second optical surface 114 may move at a second rate, and shadows produced by contamination particles on third optical surface 116 may move at a third rate. In an optical system that uses a greater or lesser number of optical surfaces, the movement of light source 110 by light source controller 130 produces shadows that may move at a rate associated with each optical surface. Accordingly, shadow movement is unique to each optical surface.

In an alternate embodiment of the present invention, light source 110 is comprised of a plurality of individual non-coherent light sources. In this embodiment, the light sources of the plurality are provided in an two-dimensional array. The array may cover an area similar to the range over which light source controller 130 moves light source 110 in the previously described embodiment. In this embodiment, rather than moving a single small light source, each light source of the plurality is individually illuminated and shadows representing the contamination particles on each of the optical surfaces are identified and tracked. As each light source of the plurality is individually illuminated, shadows from contamination particles on each of the optical surfaces change position at different rates. Accordingly, shadows on detector array 118 may be separately identified for each of the optical surfaces.

Figure 2:
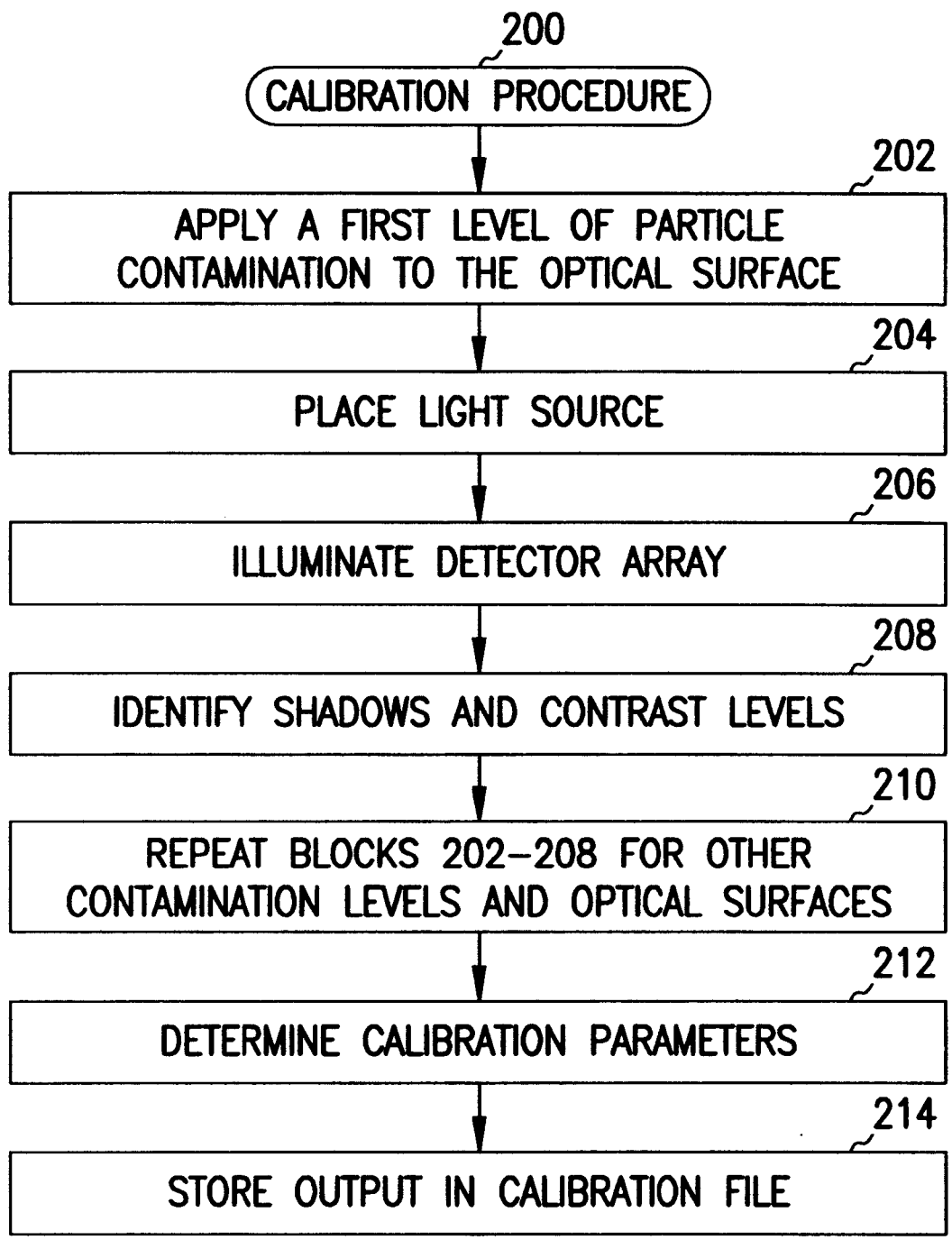
FIG. 2 is a flow chart of a calibration procedure in accordance with an embodiment of the present invention.

FIG. 2 is a flow chart of a calibration procedure in accordance with an embodiment of the present invention. Procedure 200, in general, is used to generate calibration parameters for various known particle contamination levels and may be used for a specific optical system configuration. The optical system used for procedure 200 may be a special optical system used for calibration and test purposes or may be an actual optical system destined for the field. The calibration parameters may be used for measuring particle contamination levels of optical systems in accordance with the various embodiments of the present invention. Procedure 200 may be used to determine calibration parameters for optical systems having one or more optical surfaces, and is suitable for determining calibration parameters for optical system 100 (FIG. 1).

In block 202, a first particle contamination level is applied to an optical surface. The first particle contamination level may be a contamination level specified in Mil. Std. 1246A for example, or may be any known particle contamination level. In one embodiment of the present invention, block 202 uses particle contamination level 300 specified in Mil. Std. 1246A which, for example, requires less than one particle per square foot having a diameter greater than 300 microns.

In block 204, a non-coherent light source is placed in front of the optical surface and a detector array is positioned at a focal plane of the optical surface. The light source and detector array, as well as their positioning in relation to the optical surface represent a calibration system configuration which should correspond with an actual optical system configuration for which calibration parameters are desired. In block 206, the light source is turned on and the detector array is illuminated, and in block 208, shadows of various contrast levels are identified and recorded. It should be noted that a coherent light source is not suitable for use herein because, for example, reflections off the particles may not provide suitable shadows on the detector array, but may result in an interference pattern that may be difficult to quantify.

In block 210, blocks 202–208 are repeated for other particle contamination levels. For example, in block 202, a second contamination level is applied to the optical surface, such as particle contamination level 400 specified in Mil. Std. 1246A, and in block 206, the light source is turned on illuminating the detector array. In block 208, the shadows of varying contrast levels are identified and recorded for this second particle contamination level. Block 210 may be repeated for each particle contamination level desired. The number of particle contamination levels preferably include at least particle contamination levels 300, 400 and 500 specified in Mil. Std. 1246A. In the case when the optical system includes more than one optical surface, block 210 may be performed for each of the optical surfaces.

In block 212, calibration parameters are determined. In block 212, the contrast levels from block 208 for each contamination levels are quantified and correlated with the corresponding contamination level and stored in block 214 as a calibration file. Accordingly, when particle contamination measurements are performed on an optical system similar to the calibration system configuration, the calibration file may be used to correlate shadow contrast levels with particle contamination levels for an actual optical system.

In embodiments of the present invention that measure particle contamination on several optical surfaces, procedure 200 may be repeated using a calibration system configuration that includes several representative optical surfaces. In these embodiments, particle contamination levels are applied to each one of the surfaces, one at a time in accordance with procedure 200. Each optical surface which is not being measured should be substantially free of contamination particles during the performance of procedure 200. In addition, procedure 200 may include additional blocks to provide for moving the non-coherent light source so that a rate of movement of the shadows can be measured to distinguish the shadows from each optical surface. The rate of shadow movement data may be stored with the calibration data.

Figure 3:
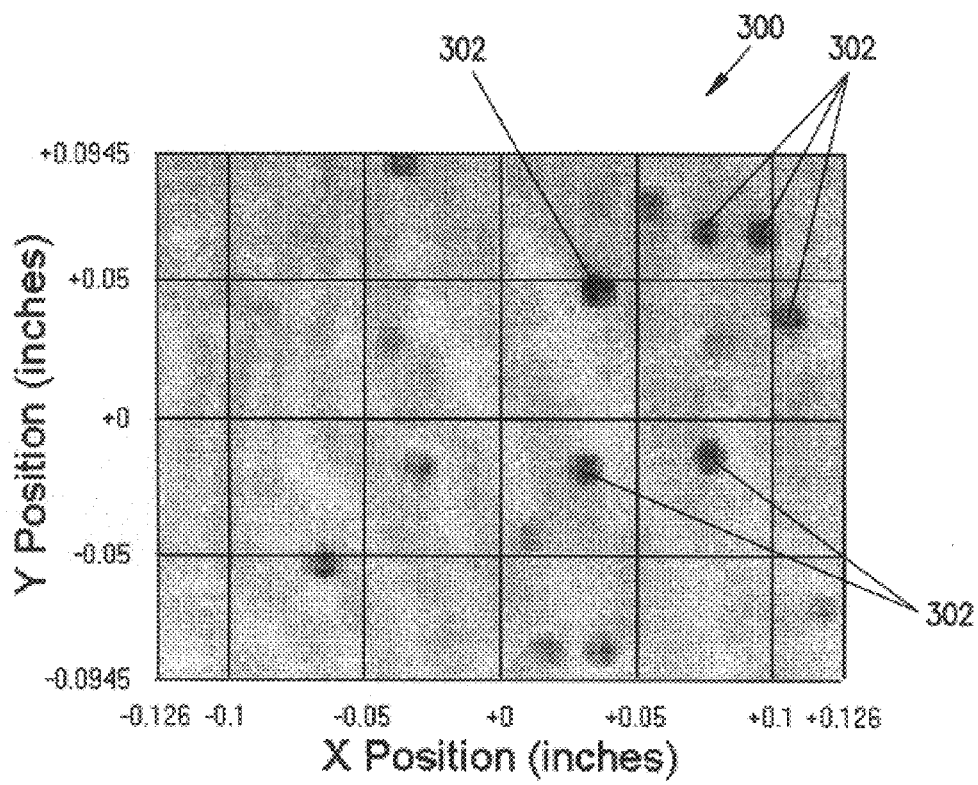
FIGS. 3–5 illustrate irradiance distributions on a detector array for various contamination levels in accordance with embodiments of the present invention.
Figure 4:
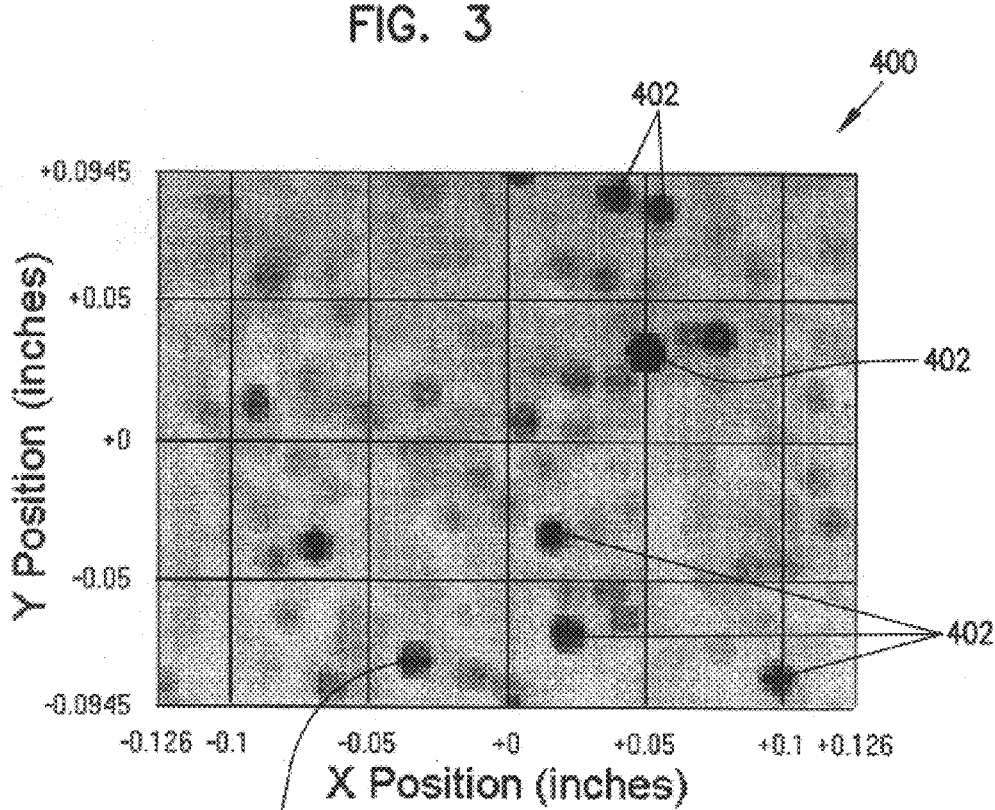
Figure 5:
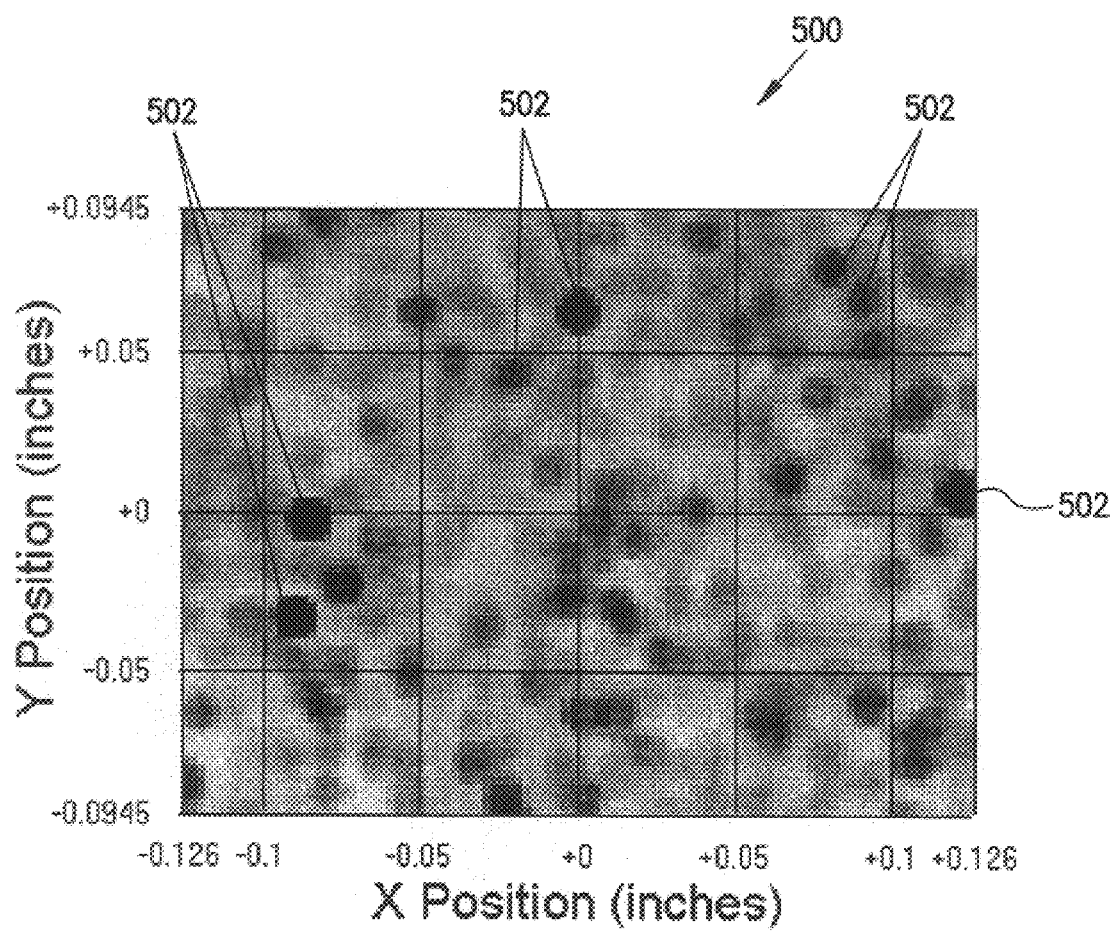

FIGS. 3–5 illustrate irradiance distributions on a detector array for various contamination levels in accordance with embodiments of the present invention. Irradiance distribution 300 (FIG. 3) represents a Level 300 particle contamination as specified in Mil. Std. 1246A, irradiance distribution 400 (FIG. 4) represents a Level 400 particle contamination as specified in Mil. Std. 1246A, and irradiance distribution 500 (FIG. 5) represents a Level 500 particle contamination as specified in Mil. Std. 1246A. The contrast levels of shadows illustrated in FIGS. 3–5 are examples that may be used in block 208 of procedure 200 (FIG. 2) to correlate particle contamination levels with shadow contrast.

Shadows 302, for example, represent particles that provide Level 300 particle contamination and have a certain contrast level. It should be noted that the contrast level of shadows 302 is less than the contrast level of shadows 402 (FIG. 4) which represent particles that provide, for example, a Level 400 particle contamination level. In addition, the contrast level of shadows 502 (FIG. 5) is greater than the contrast level of shadows 402 and 302. Shadows 502 represent particles that provide, for example, a Level 500 particle contamination level.

Figure 6:
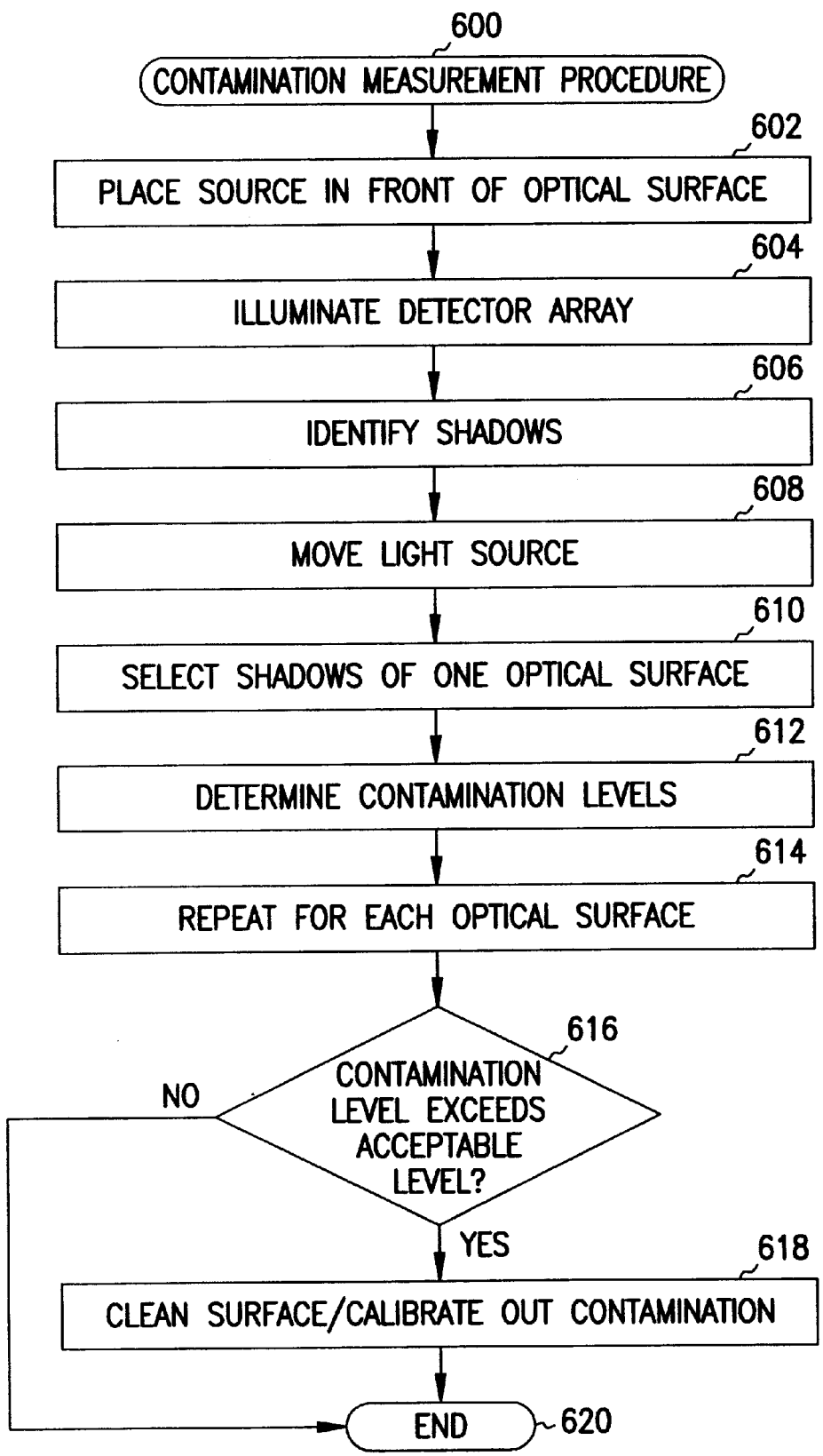
FIG. 6 is a flow chart of a particle contamination measurement procedure in accordance with an embodiment of the present invention.

FIG. 6 is a flow chart of a particle contamination measurement procedure in accordance with an embodiment of the present invention. Contamination measurements in accordance with the embodiments described by procedure 600 may be performed on optical systems that are in the field and may be inaccessible, as well as performed on optical systems with accessible optical surfaces. For example, in accordance with procedure 600, particle contamination may be measured on optical surfaces of remotely located sensors, or optical systems of orbiting satellites. Additionally, in accordance with procedure 600, particle an contamination may be measured on optical surfaces during, for example, the test and assembly phases of such optical systems. Desirably, procedure 600 is able to detect contamination particles as small as 50 to 100 microns in diameter and even smaller.

In block 602, a non-coherent light source is placed in front of an optical surface of an optical system. When the optical system includes several optical surfaces that are part of a light reflecting path, the light source is placed in front of the first optical surface. The light source is placed in a position close enough to the first optical surface to illuminate a two-dimensional detector array placed at a focal plane of the optical surface(s). The light source may be a small non-coherent light source, such as a point light source. Although the various embodiments of the present invention are described with the use of non-coherent light sources, it should be noted that other types of non-coherent radiation may also be suitable for use with the present invention.

In block 604, the two-dimensional detector array is illuminated by turning on the non-coherent light source. The detector array, located at a focal plane of the optical surface(s), may be a detector array used primarily for particle contamination measurements. In an alternate embodiment, the detector array may be the operational detector array used in the end-use operational environment of the optical system. For example, referring to FIG. 1, when system 100 is part of a space based optical sensor, detector array 118 may be the actual detector used for receiving optical data as well as the detector used for particle contamination measurements. On the other hand, in the alternate embodiment, when detector array 118 is primarily used for particle contamination measurements, system 100 includes an operational detector array (not shown) for detecting the operation system optical data.

In block 606, shadows on the detector array are identified. As part of block 606, shadows of various contrast levels are identified by processing equipment coupled to the detector array. The shadows represent contamination particles the optical surface. In systems that include more than one optical surface, the shadows represent contamination particles on all of the optical surfaces. The differing contrast levels of the shadows correspond with different size contamination particles.

In block 608, light source is moved. In one embodiment, the light source remains illuminated and a light source controller slightly changes the position of the light source. Systems that include more than one optical surface produce a set of shadows on the surface of the detector array for each optical surface. The shadows of each set move at different rates depending on the relationship between the optical surfaces. The rate of movement of the shadows of each set is used to distinguish the shadows for each optical surface. Slight movement of the light source is often all that is required to generate sufficient movement of the shadows. In systems that include only one optical surface for which particle contamination level measurements are performed, procedure 600 may refrain from performing block 608.

In block 610, the shadows from at least one of the optical surfaces are selected and tracked. Processing equipment coupled with the detector array may, for example, use a digital filtering technique to stabilize the shadow pattern of the first set to analyze particle contamination on one of the surfaces.

In block 612, contamination levels for each optical surface are determined based on the distribution of shadows and the contrast levels of the shadows on the detector array for the selected set of shadows. An autocorrelation function, for example, may be used, to correlate specific contamination levels, and may utilize calibration data to help determine an actual particle contamination level. The calibration data may be generated, for example, through the performance of procedure 200 (FIG. 2) using a representative calibration test system. Procedure 200 may include generating calibration data to identify which sets of shadows correspond with each of the optical surfaces when measurements are performed on systems that have more than one optical surface.

In one embodiment, block 612 includes determining the number of contamination particles for each size range of particles by counting the number of shadows of different contrast levels. For example, the shadows of contamination particles having a diameter of between 100 and 150 microns are identified by their contrast level and counted, and the shadows of contamination particles having a diameter of between 150 and 200 microns are identified by their respective contrast level and counted.

Block 614 is performed for optical systems that include more than one optical surface. In block 614, blocks 604 through 612 are repeated for each optical surface. In other words, the set of shadows resulting from particles of each optical surface is separately identified and analyzed, and a particle contamination level is determined for each optical surface.

In block 616, the particle contamination levels measured in block 612 are compared to acceptable levels, and when the contamination levels exceed an acceptable level, block 618 is performed. When the contamination levels do not exceed acceptable levels, block 620 is performed. In block 618, the optical surfaces may be cleaned with an optical surface cleaning system. When the optical system is in end-use and inaccessible, the cleaning may include a plasma cleaning process, a carbon-dioxide jet spray cleaning process, or other cleaning process using cleaning equipment resident with the optical system. When the optical system is accessible, for example, the cleaning may include any of several cleaning methods which could be performed manually or by automated means.

In an alternate embodiment, in block 618, the particle contamination levels are calibrated out. For example, the particle contamination levels of the optical surfaces are compensated for by the system processing equipment in an effort to improve system performance.

In one embodiment of the present invention, when the particle contamination levels for each optical surface are determined at the completion of block 614, the contamination level data may be provided or transmitted to a system operator and blocks 616 and 618 may not be performed. In block 620, contamination measurement procedure 600 is completed. Procedure 600 may be repeated on a regular basis as part of a routine maintenance program on a remote optical sensor or space telescope, or may be repeated at various stages during assembly and test of such systems.

It should be noted that procedure 600 provides only an estimate of the average particle contamination based on the portion of the optical surfaces for which the shadows occur on the detector array. In an alternate embodiment of the present invention, block 608 includes changing the position of the light source sufficiently to provide particle contamination shadows on the detector array from a significant portion or all of the area of the optical surfaces. In this alternate embodiment, a more accurate actual particle contamination level can be obtained. In addition, in this alternate embodiment, defects in the optical surfaces are more easily identified. It also should be noted that several of the blocks of procedure 600 may be automated and performed concurrently, and may be performed in a different order than the order illustrated.

Thus, a system and method for performing in-situ particle contamination level measurements has been described. The system and method allow for particle contamination level measurements on optical surfaces that are in the field and inaccessible, as well as optical surfaces that are accessible and configured in a system. The system and method provide particle contamination measurements on each of several optical surfaces in optical systems that include more than one optical surface. In one embodiment, the system and method compensate for the particle contamination levels measured on the optical surfaces, for example, to achieve improved system performance. In yet another embodiment, the system and method provide for cleaning the optical surfaces when particle contamination levels exceed a predetermination level, for example to improve system performance.

The foregoing description of the specific embodiments reveals the general nature of the invention sufficiently that others can, by applying current knowledge, readily modify and/or adapt it for various applications without departing from the generic concept, and therefore such adaptations and modifications are intended to be comprehended within the meaning and range of equivalents of the disclosed embodiments.

It is to be understood that the phraseology or terminology employed herein is for the purpose of description and not of limitation. Accordingly, the invention is intended to embrace all such alternatives, modifications, equivalents and variations as fall within the spirit and broad scope of the appended claims.

What is claimed is:

1. A method for measuring particle contamination on an optical surface comprising:

illuminating a detector with light provided by a non-coherent light source, the light traveling through a path that includes the optical surface;

identifying shadows on the detector, the shadows being indicative of particle contamination of the optical surface; and estimating a particle contamination level for the optical surface based on contrast levels of the shadows identified on the detector.

2. The method as claimed in claim 1 wherein the optical surface is a first of a plurality of optical surfaces and wherein the detector is illuminated with light from the non-coherent light source traveling through a path that includes the plurality of optical surfaces, the method further comprising changing a position of the non-coherent light source to distinguish shadows caused by particle contamination on the first of the optical surfaces from shadows caused by particle contamination on other optical surfaces of the plurality.

3. The method as claimed in claim 1 further comprising cleaning the optical surface when the particle contamination level exceeds a predetermined level.

4. The method as claimed in claim 1 further comprising calibrating optical processing equipment to compensate for the estimated particle contamination level.

5. The method as claimed in claim 1 wherein the optical surface is a reflective surface oriented to reflect light through the path to the detector.

6. The method as claimed in claim 5 wherein the optical surface comprises part of an optical telescope, and wherein the method further comprises cleaning the optical surface when the particle contamination level exceeds a predetermined level.

7. The method as claimed in claim 1 wherein the optical surface comprises a refractive optical surface oriented to refract light through the path to the detector, and wherein the illuminating comprises illuminating the detector with light refracted by the optical surface.

8. The method as claimed in claim 1 wherein the optical surface is a first of a plurality of optical surfaces, the method further comprising:

providing a plurality of non-coherent light sources, each light source having a slightly different position relative to the optical surfaces; and illuminating the detector separately with each non-coherent light source of the plurality to produce first sets of shadows on the detector caused by particle contamination on the first of the optical surfaces and second sets of shadows on the detector caused by particle contamination on a second of the optical surfaces; and distinguishing shadows of the first set from shadows of the second set by identifying different changed positions for the shadows which result from separate illumination of each non-coherent light source of the plurality.

9. A method for measuring particle contamination on an optical surface comprising:

illuminating a detector with light provided by a non-coherent light source, the light traveling through a path that includes the optical surface;

identifying shadows on the detector, the shadows being indicative of particle contamination of the optical surface; and estimating a particle contamination level for the optical surface based on contrast levels of the shadows identified on the detector, wherein the optical surface is a first of a plurality of optical surfaces and wherein the detector is illuminated with light from the non-coherent light source traveling through a path that includes the plurality of optical surfaces, the method further comprising changing a position of the non-coherent light source to distinguish shadows caused by particle contamination on the first of the optical surfaces from shadows caused by particle contamination on other optical surfaces of the plurality, and wherein the shadows on the detector are comprised of a first set of shadows indicative of particle contamination on the first of the optical surfaces, and a second set of shadows indicative of particle contamination on a second of the optical surfaces, wherein changing the position of the non-coherent light source changes a position of the first set of shadows to a first changed position on the detector and changes a position of the second set of shadows to a second changed position on the detector, and wherein the method further comprises:
  identifying the first and second changed positions to distinguish the first set of shadows from the second set of shadows;
  estimating a particle contamination level for the first of the optical surfaces based on contrast levels of shadows of the first set; and
  estimating a particle contamination level for the second of the optical surfaces based on contrast levels of shadows of the second set.

10. The method as claimed in claim 9 wherein the shadows on the detector include a third set of shadows indicative of particle contamination on a third of the optical surfaces, wherein changing the position of the non-coherent light source changes a position of the third set of shadows to a third changed position on the detector, and wherein the method further comprises:
  identifying the third changed position to distinguish the third set of shadows from the first and second sets of shadows; and
  estimating a particle contamination level for the third of the optical surfaces based on contrast levels of shadows of the third set.

11. A method for measuring particle contamination on an optical surface comprising:
  illuminating a detector with light provided by a non-coherent light source, the light traveling through a path that includes the optical surface;
  identifying shadows on the detector, the shadows being indicative of particle contamination of the optical surface; and
  estimating a particle contamination level for the optical surface based on contrast levels of the shadows identified on the detector,
  wherein shadows of greater contrast levels on the detector are indicative of larger size particles than shadows of lesser contrast levels, and wherein estimating the particle contamination level for the optical surface further comprises:
    comparing the contrast level of shadows on the detector with contrast levels in a calibration file to determine particle sizes associated with the shadows; and
    determining an average particle contamination level for the optical surface based on a number of particles within predetermined ranges of sizes.

12. A method of identifying defects on optical surfaces comprising:
  illuminating a detector with light provided by a non-coherent light source, the light traveling through a path that includes the optical surfaces;
  identifying shadows on the detector, the shadows being indicative of defects in the optical surfaces; and
  moving the non-coherent light source to distinguish different sets of shadows, wherein a first set of shadows is indicative of defects on a first of the optical surfaces and a second set of shadows is indicative of defects on a second of the optical surfaces.

13. The method as claimed in claim 12 further comprising estimating a defect level for the first optical surface based on contrast levels of the shadows identified for the first optical surface.

14. The method as claimed in claim 12 wherein the optical surfaces comprise a reflective optical surface to reflect the light provided by the non-coherent light source to illuminate the detector.

15. The method as claimed in claim 12 wherein the optical surfaces comprise a refractive optical surface to refract the light provided by the non-coherent light source to illuminate the detector.

16. The method as claimed in claim 12 wherein the optical surfaces comprise a combination of reflective and refractive optical surfaces to reflect and refract the light, respectively, through the path to illuminate the detector.

17. A system for measuring particle contamination on an optical surface comprising:
  a non-coherent light source to illuminate a detector with non-coherent light traveling through a path that includes the optical surface;
  processing equipment to identify shadows on the detector, the shadows being indicative of particle contamination on the optical surface; and
  a particle contamination level analyzer to estimate a particle contamination level for the optical surface based on contrast levels of the shadows identified for the optical surface.

18. The system as claimed in claim 17 wherein the optical surface is a first of a plurality of optical surfaces, the system further comprising a light source controller to change a position of the non-coherent light source, the processing equipment to distinguish shadows caused by particle contamination on the first of the optical surfaces from shadows caused by particle contamination on other of the optical surfaces of the plurality based on movement of the shadows.

19. The system as claimed in claim 17 further comprising an optical surface cleaning system to clean the optical surface when the particle contamination level exceeds a predetermined level.

20. The system as claimed in claim 17 wherein the processing equipment compensates for the particle contamination level.

21. The system as claimed in claim 17 wherein the optical surface is a reflective surface oriented to reflect light through the path to the detector.

22. The system as claimed in claim 17 wherein the optical surface comprises part of an optical telescope, and wherein the system further comprises an optical surface cleaning system to clean the optical surface when the particle contamination level exceeds a predetermined level.

23. The system as claimed in claim 17 wherein the optical surface is a refractive optical surface to refract light through the path to the detector.

24. The system as claimed in claim 17 wherein the optical surface is a first of a plurality of optical surfaces, the system further comprising:
   a plurality of non-coherent light sources, each light source having a slightly different position relative to the optical surfaces; and
   a light source controller to separately illuminate the detector with each non-coherent light source of the plurality to produce first sets of shadows on the detector caused by particle contamination on the first of the optical surfaces and second sets of shadows on the detector caused by particle contamination on a second of the optical surfaces,
   the processing equipment to distinguish shadows of the first set from shadows of the second set by identifying different changed positions for the shadows which result from separate illumination of each non-coherent light source of the plurality.

25. The system as claimed in claim 17 further comprising a plurality of optical surfaces, the plurality including a combination of reflective and refractive optical surfaces to reflect and refract the light, respectively, through the path to illuminate the detector.

26. A system for measuring particle contamination on an optical surface comprising:
   a non-coherent light source to illuminate a detector with non-coherent light traveling through a path that includes the optical surface;
   processing equipment to identify shadows on the detector, the shadows being indicative of particle contamination on the optical surface; and
   a particle contamination level analyzer to estimate a particle contamination level for the optical surface based on contrast levels of the shadows identified for the optical surface,
   wherein the optical surface is a first of a plurality of optical surfaces, the system further comprising a light source controller to change a position of the non-coherent light source, the processing equipment to distinguish shadows caused by particle contamination on the first of the optical surfaces from shadows caused by particle contamination on other of the optical surfaces of the plurality based on movement of the shadows, and
   wherein the shadows on the detector include a first set of shadows indicative of particle contamination on the first of the optical surfaces, and a second set of shadows on the detector indicative of particle contamination on a second of the optical surfaces, and wherein a changed position of the non-coherent light source changes a position of the first set of shadows to a first changed position on the detector and changes a position of the second set of shadows to a second changed position on the detector,
   wherein the processing equipment identifies the first and second changed positions to distinguish the first set of shadows from the second set of shadows, and
   wherein the particle contamination level analyzer estimates the particle contamination level for the first optical surface based on contrast levels of shadows of the first set and estimates the particle contamination level for the second optical surface based on contrast levels of shadows of the second set.

27. The system as claimed in claim 26 wherein the shadows on the detector include a third set of shadows indicative of particle contamination on a third of the optical surfaces;
   the light source controller changes the position of the non-coherent light source to change a position of the third set of shadows to a third changed position on the detector;
   the processing equipment identifies the third changed position to distinguish the third set of shadows from the first and second sets of shadows; and
   the contamination level analyzer estimates a particle contamination level for the third of the optical surfaces based on contrast levels of shadows of the third set.

28. A system for measuring particle contamination on an optical surface comprising:
   a non-coherent light source to illuminate a detector with non-coherent light traveling through a path that includes the optical surface;
   processing equipment to identify shadows on the detector, the shadows being indicative of particle contamination on the optical surface; and
   a particle contamination level analyzer to estimate a particle contamination level for the optical surface based on contrast levels of the shadows identified for the optical surface,
   wherein shadows on the detector having greater contrast levels are indicative of larger size particles than shadows of lesser contrast levels, and wherein the particle contamination level analyzer estimates- an average particle contamination level for the optical surface by comparing the contrast level of the shadows on the detector with contrast levels in a calibration file to determine particle sizes associated with shadows, the average particle contamination level for the optical surface being based on a number of particles within predetermined ranges of sizes.

* * * * *